(12) United States Patent
Abe

(10) Patent No.: US 8,126,113 B2
(45) Date of Patent: Feb. 28, 2012

(54) X-RAY DIAGNOSIS APPARATUS

(75) Inventor: Shingo Abe, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 220 days.

(21) Appl. No.: 12/694,554

(22) Filed: Jan. 27, 2010

(65) Prior Publication Data

US 2010/0189217 A1 Jul. 29, 2010

(30) Foreign Application Priority Data

Jan. 29, 2009 (JP) ................................ 2009-018603

(51) Int. Cl.
*G01N 23/04* (2006.01)
(52) U.S. Cl. ........................................................ 378/62
(58) Field of Classification Search .................... 378/62, 378/98, 98.11, 98.12, 193–198; 382/128–132; 600/407, 425, 427, 431
See application file for complete search history.

(56) References Cited

U.S. PATENT DOCUMENTS

| 2008/0097187 A1 | 4/2008 | Gielen et al. ................. 600/409 |
| 2008/0234575 A1 | 9/2008 | Klingenbeck-Regn et al. ............................ 600/431 |
| 2010/0104167 A1 | 4/2010 | Sakaguchi et al. |

FOREIGN PATENT DOCUMENTS

| DE | 10 2005 012 985 A1 | 7/2006 |
| JP | 4-48452 | 8/1992 |

*Primary Examiner* — Courtney Thomas
(74) *Attorney, Agent, or Firm* — Oblon, Spivak, McClelland, Maier & Neustadt, L.L.P.

(57) ABSTRACT

A storage unit stores a plurality of vectors and a plurality of past electrocardiographic phases in association with each other. Each of the vectors is a vector from a past reference point to a past objective point. A Reference point specifying unit specifies a current reference point on a current image. An electrocardiograph detects a current electrocardiographic phase associated with the current image. A vector specifying unit specifies a specific vector associated with a past electrocardiographic phase corresponding to the detected current electrocardiographic phase among the plurality of vectors. Objective point calculation unit calculates a position of a current objective point on the current image based on the specified vector and the position of the current reference point. A display unit displays the position of the current objective point on the current image.

14 Claims, 11 Drawing Sheets

Past image
(contrast-enhanced image generated before treatment)

Specifying of reference point 58 on past image

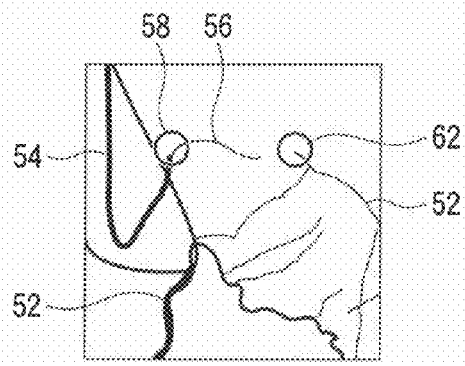
FIG. 5  Designation of objective point 62 on past image
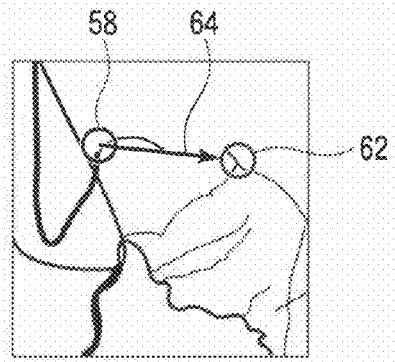
FIG. 6  Calculation of vector 64 from past reference point 58 to past objective point 62
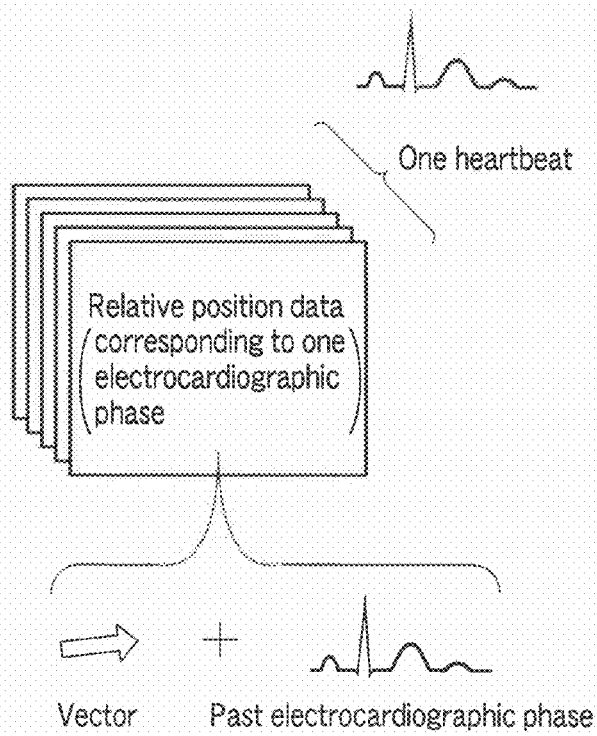
FIG. 7

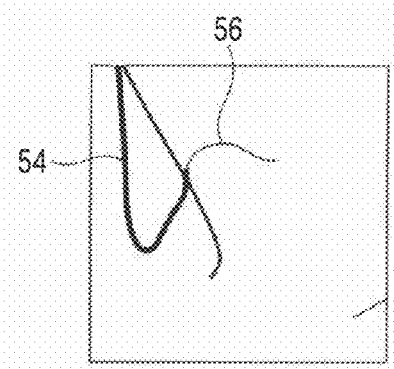
FIG. 9  Current image
(non-contrast-enhanced image generated during treatment)
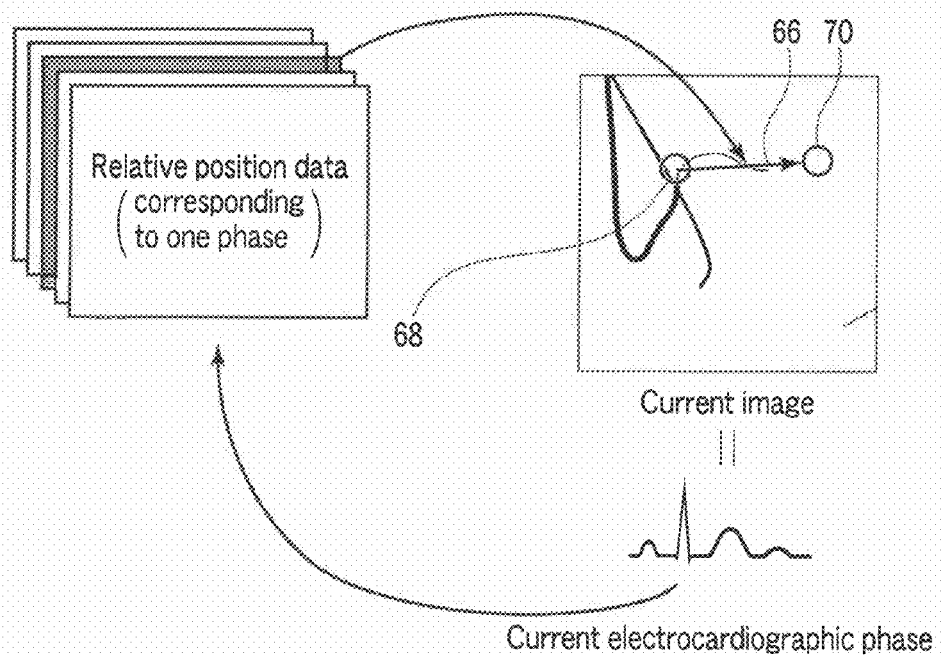
FIG. 10  Calculation of position of objective point 70 on current image
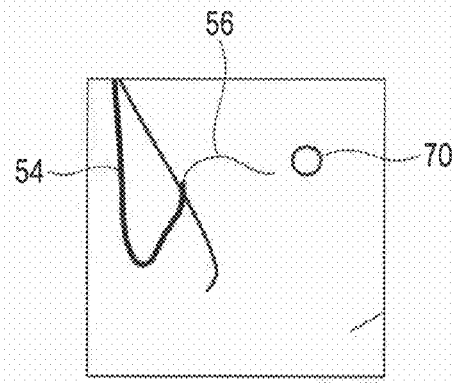
FIG. 11  Display of current image with highlighted current objective point 70

Comparison between display accuracies by using current images A and C
in identical electrocardiographic phases and identical respiratory phases

|  | Difference between coordinates (A and C) | Distance [pixel] | Difference between vectors (A and C) | Distance [pixel] |
|---|---|---|---|---|
| Distal end of catheter | (−2, −14) | 14.14 | Reference | Reference |
| Exit | (−6, −13) | 14.32 | (−4, 1) | 4.12 |

F I G. 13

Comparison between display accuracies by using current images A and B
in identical electrocardiographic phases and different respiratory phases

|  | Difference between coordinates (A and B) | Distance [pixel] | Difference between vectors (A and B) | Distance [pixel] |
|---|---|---|---|---|
| Distal end of catheter | (0, 17) | 17 | Reference | Reference |
| Exit | (2, 18) | 18.11 | (2, 1) | 2.24 |

F I G. 14

Comparison between display accuracies by using current images A and D
in identical electrocardiographic phases and different respiratory phases

|  | Difference between coordinates (A and D) | Distance [pixel] | Difference between vectors (A and D) | Distance [pixel] |
|---|---|---|---|---|
| Distal end of catheter | (−3, −14) | 14.32 | Reference | Reference |
| Exit | (−5, −13) | 13.93 | (−2, 1) | 2.24 |

F I G. 15

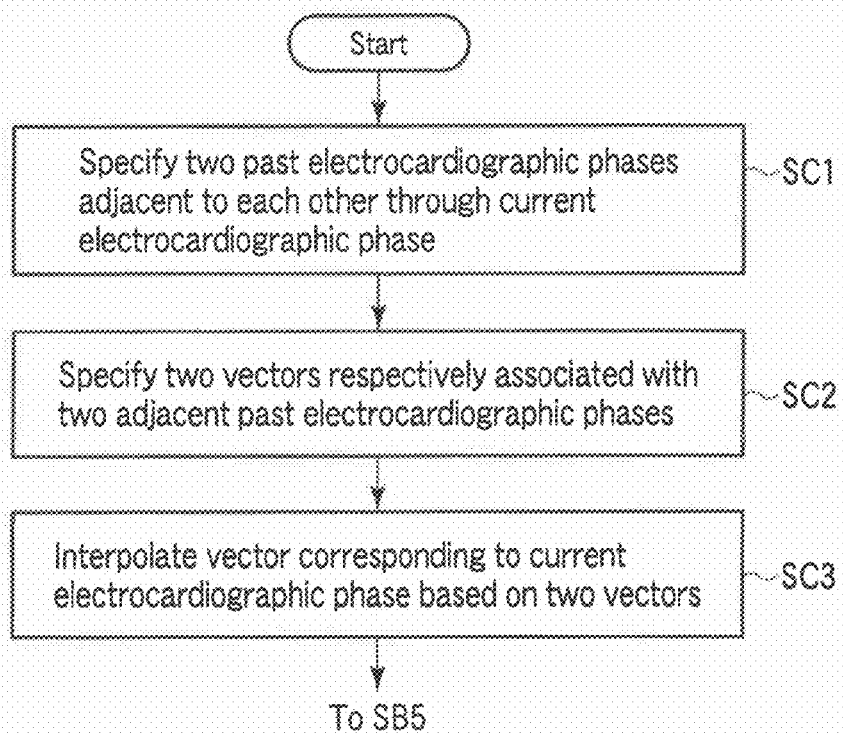
F I G. 18
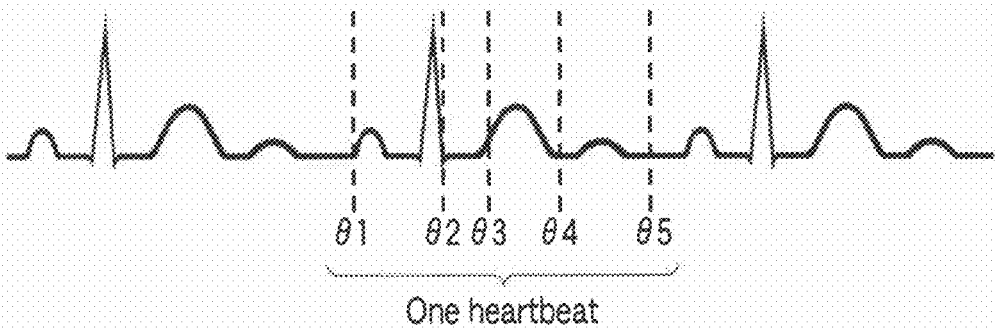
F I G. 19

X-RAY DIAGNOSIS APPARATUS

CROSS-REFERENCE TO RELATED APPLICATIONS

This application is based upon and claims the benefit of priority from prior Japanese Patent Application No. 2009-018603, filed Jan. 29, 2009, the entire contents of which are incorporated herein by reference.

BACKGROUND OF THE INVENTION

1. Field of the Invention

The present invention relates to an X-ray diagnosis apparatus for supporting catheterization.

2. Description of the Related Art

There is available an X-ray diagnosis apparatus for supporting catheterization. One of catheterization techniques is coronary artery intervention. In coronary artery intervention, the operator manipulates a device such as a catheter under fluoroscopy while checking a stenotic region or a blood vessel shape on a contrast-enhanced image (past image). In general, a contrast-enhanced image and a fluoroscopic image (current image) are displayed on different monitors. The operator comprehends a stenotic region or a blood vessel shape on a contrast-enhanced image and the device position or the like on a fluoroscopic image by taking into consideration the movement of the heart due to pulsation or respiration while alternately referring to these contrast-enhanced and fluoroscopic images. This makes it difficult to comprehend a stenotic region, a blood vessel shape, and the position of an objective region such as a device position.

As disclosed in, for example, Jpn. Pat. Appln. KOKOKU Publication No. 04-48452, as a technique for supporting coronary artery intervention, there is available a technique of superimposing and displaying a contrast-enhanced image corresponding to one heartbeat on a fluoroscopic image by using the ECG gated imaging method. However, a large positional shift due to respiration degrades superimposition accuracy. In addition, a given portion of the heart does not necessarily remain at the same position even in identical electrocardiographic phases. Even in respiratory phases and identical electrocardiographic phases with breath holding, the superimposition accuracy is poor. For this reason, even with the use of this technique, it is still difficult to comprehend an objective region. That is, the number of times of contrast medium imaging does not decrease. In addition, the load on each subject remains heavy. Under the circumstances, there has been a strong demand for the advent of a technique that can improve the efficiency of catheterization.

BRIEF SUMMARY OF THE INVENTION

It is an object of the present invention to provide an X-ray diagnosis apparatus which improves the efficiency of catheterization.

According to a first aspect of the present invention, An X-ray diagnosis apparatus includes: an imaging unit configured to comprise an X-ray tube and a detector to obtain a first X-ray image and a second X-ray image associated with a subject in which a medical tool is inserted; a first specifying unit configured to specify a first reference point on a first medical tool area included in the first X-ray image; a designation unit configured to designate a first objective point on the first X-ray image; a first calculation unit configured to calculate a relative positional relationship between the first reference point and the first objective point; a second specifying unit configured to specify a second reference point on a second medical tool area included in the second X-ray image; a second calculation unit configured to calculate a position of a second objective point on the second X-ray image based on the relative positional relationship and the second reference point; and a display unit configured to display the second X-ray image while highlighting the position of the second objective point.

According to a second aspect of the present invention, An X-ray diagnosis apparatus includes: a storage unit configured to store a plurality of vectors and a plurality of past electrocardiographic phases in association with each other, each of the plurality of vectors being a vector from a past reference point to a past objective point included in each of a plurality of past images associated with a subject, and each of the plurality of past electrocardiographic phases being an electrocardiographic phase of the subject which is associated with a time at which the past image was obtained; an imaging unit configured to comprise an X-ray tube and a detector to obtain a current image associated with the subject; a first specifying unit configured to specify a current reference point on the current image by image processing; a detection unit configured to detect a current electrocardiographic phase associated with the current image; a second specifying unit configured to specify a specific vector associated with a past electrocardiographic phase corresponding to the detected current electrocardiographic phase among the plurality of vectors; a first calculation unit configured to calculate a position of a current objective point on the current image based on the specified vector and the position of the current reference point; and a display unit configured to display the position of the current objective point on the current image.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 5 is a view for explaining past objective point designation processing performed in step SA5 in FIG. 2;

FIG. 6 is a view for explaining vector calculation processing performed in step SA6 in FIG. 2;

FIG. 7 is a view for explaining relative position data storage processing performed in step SA7 in FIG. 2;

FIG. 9 is a view showing an example of a current image acquired in step SB1 in FIG. 8;

FIG. 10 is a view for explaining current objective point position calculation processing in step SB5 in FIG. 8;

FIG. 11 is a view for explaining current objective point explicit display processing in step SB6 in FIG. 8;

FIG. 13 is a view showing the comparison result on objective point display accuracy between the technique according to this embodiment and the prior art;

FIG. 14 is a view showing the comparison result on objective point display accuracy between the technique according to this embodiment and the prior art;

FIG. 15 is a view showing the comparison result on objective point display accuracy between the technique according to this embodiment and the prior art;

FIG. 18 is a flowchart showing a typical procedure for current objective point display processing performed under the control of a system control unit in FIG. 17; and FIG. 19 is a view showing an example of electrocardiographic phases selected in the modification.

DETAILED DESCRIPTION OF THE INVENTION

An X-ray diagnosis apparatus according to an embodiment of the present invention will be described below with reference to the views of the accompanying drawing. An outline of this embodiment will be described first.

An X-ray diagnosis apparatus according to this embodiment is used in catheterization such as coronary artery intervention. In coronary artery intervention, X-ray images with blood vessels being contrast-enhanced with a contrast medium in advance (to be referred to as past images hereinafter) are acquired in advance. Past images are acquired at, for example, an imaging frame rate of 7.5 to 30 frames/sec. A plurality of past images corresponding to at least one heartbeat are acquired at this imaging frame rate. A contrast medium is injected into a subject through a catheter inserted in it. Past images therefore depict medical tools such as a catheter, wire, and stent. In addition, such an image depicts a treatment region such as a stenotic region contrast-enhanced with a contrast medium. At the stage of treatment after the acquisition of past images, X-ray images without any contrast medium (to be referred to as current images hereinafter) are acquired in real time. The operator advances a medical tool to the treatment region while referring to past and current images displayed on different monitors. A current image depicts the medical tool. However, current images depict no treatment region such as a stenotic region because no contrast medium is injected during the acquisition of current images.

The X-ray diagnosis apparatus according to this embodiment calculates the position of a objective point on a current image based on a vector from a reference point on the medical tool depicted on a past image to a objective point such as a treatment region, and displays a current image while highlighting the calculated position of the objective point.

As the medical tools according to this embodiment, any kinds of medical tools inserted into the body, e.g., a catheter, guide wire, and stent, can be used. For the sake of a concrete description to be made below, assume that medical tools to be used are a catheter and a wire.

Figure 1:
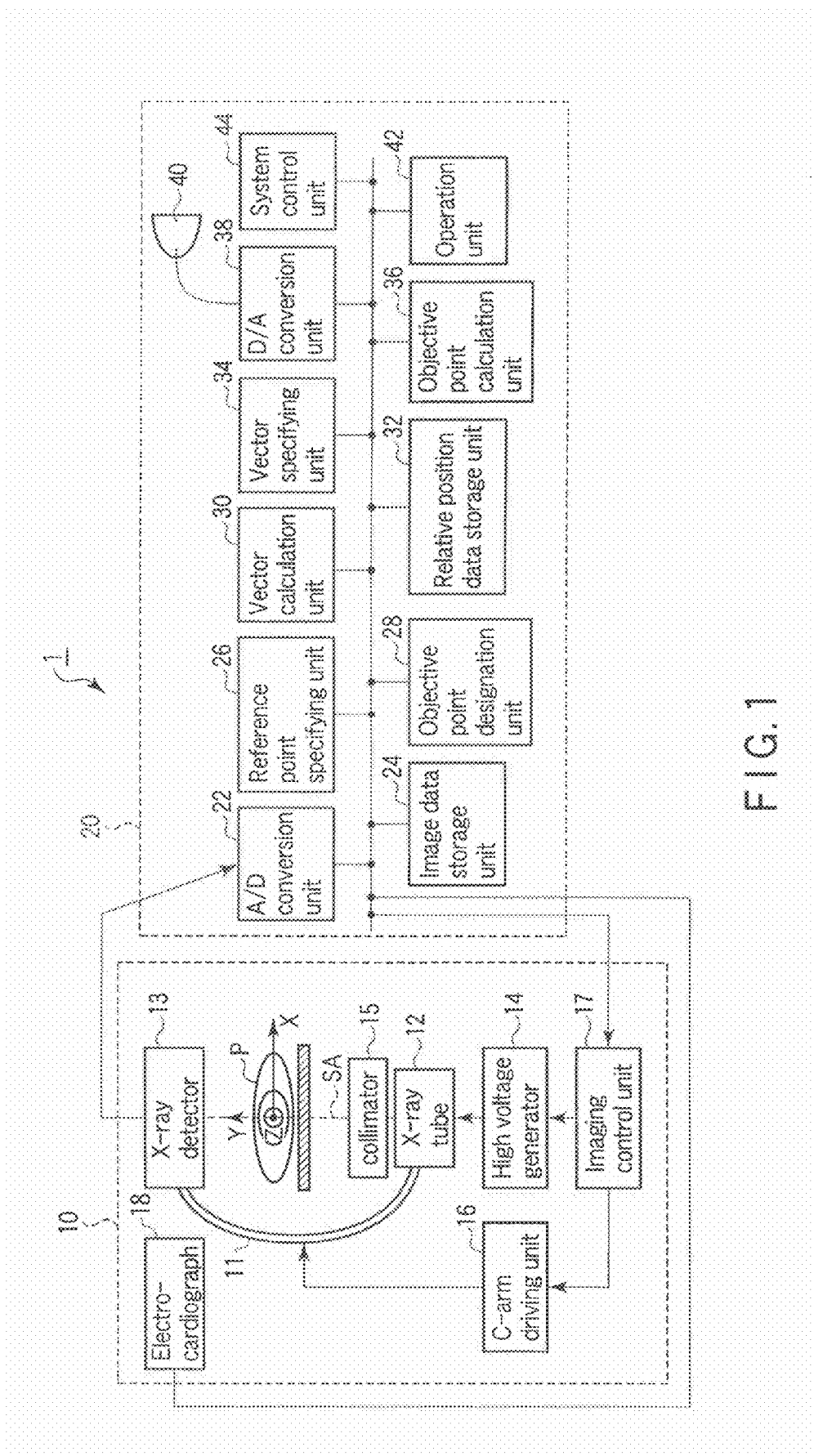
FIG. 1 is a block diagram showing the arrangement of an X-ray diagnosis apparatus according to an embodiment of the present invention.

FIG. 1 is a block diagram showing the arrangement of the X-ray diagnosis apparatus according to this embodiment. As shown in FIG. 1, an X-ray diagnosis apparatus 1 includes an imaging unit 10 and an image processing apparatus 20.

As shown in FIG. 1, the imaging unit 10 has a C-arm 11. An X-ray tube 12 and an X-ray detector 13 are mounted on the C-arm 11. The X-ray tube 12 generates X-rays upon reception of a high voltage from a high voltage generator 14. An collimator 15 is attached to the X-ray tube 12. The collimator 15 limits the irradiation field of X-rays generated from the X-ray tube 12.

The X-ray detector 13 outputs an image signal by detecting the X-rays generated from the X-ray tube 12 and transmitted through a subject P. The X-ray detector 13 includes a flat panel detector (FPD) having a plurality of semiconductor detection elements arranged in the form of a matrix. Note that the X-ray detector 13 can include a combination of an image intensifier and a TV camera instead of the FPD.

The C-arm 11 can rotate along the three orthogonal axes, i.e., X-, Y-, and Z-axes, so as to freely change the imaging angle relative to the subject P. Typically, an imaging angle is defined as the intersection angles of an imaging axis SA relative to the three orthogonal axes, i.e., the X-, Y-, and Z-axes. Conventionally, an imaging angle is defined as angles at the first oblique position (RAO), second oblique position (LAO), third oblique position (CRA), and fourth oblique position (CAU). The imaging axis SA is defined as a straight line extending from the X-ray focus of the X-ray tube 12 and passing through the detection surface center of the X-ray detector 13. Typically, the Z-axis is defined as an axis almost coinciding with the body axis of the subject P. The Z-, Y-, and X-axes intersect at an isocenter (fixed imaging point). The C-arm 11 moves to an imaging angle in accordance with a driving signal from a C-arm driving unit 16.

An imaging control unit 17 radiographs an imaging region of the subject P by controlling the high voltage generator 14 and the C-arm driving unit 16 under the control of a system control unit 44 (to be described later). More specifically, the imaging control unit 17 controls the high voltage generator 14 to make the X-ray tube 12 generates a predetermined dose of X-rays. The imaging control unit 17 controls the C-arm driving unit 16 to position the C-arm 11 at a predetermined imaging angle.

The imaging unit 10 includes an electrocardiograph 18. The electrocardiograph 18 detects an electrocardiographic phase associated with a subject during catheterization. In this case, an electrocardiographic phase corresponds to an elapsed time from the occurrence time of a characteristic wave of an electrocardiographic complex. As a characteristic wave, an R wave which is most easily detected on an electrocardiographic complex is preferably used. The electrocardiograph 18 supplies the data of the detected electrocardiographic phase to the image processing apparatus 20. An electrocardiographic phase during the acquisition of past images and an electrocardiographic phase during the acquisition of current images will be respectively referred to as a past electrocardiographic phase and a current electrocardiographic phase hereinafter.

The image processing apparatus 20 includes an A/D conversion unit 22, an image data storage unit 24, a reference point specifying unit 26, a objective point designation unit 28, a vector calculation unit 30, a relative position data storage unit 32, a vector specifying unit 34, a objective point calculation unit 36, a D/A conversion unit 38, a display unit 40, an operation unit 42, and the system control unit 44.

The A/D conversion unit 22 is electrically connected to the X-ray detector 13. The A/D conversion unit 22 generates X-ray image data by digitizing the image signal output from the X-ray detector 13. As described above, during treatment, current image data is generated as X-ray image data. And at the time of contrast medium imaging before treatment, past image data is generated as X-ray image data. Current and past images can be radiographic images or fluoroscopic images.

The image data storage unit 24 stores the past image data generated by the A/D conversion unit 22 and the past electrocardiographic phase data from the electrocardiograph 18 in association with each other. The image data storage unit 24 also stores the current image data generated by the A/D conversion unit 22 and the current electrocardiographic phase data from the electrocardiograph 18 in association with each other. Note that in this embodiment, it is not always necessary to store current image data.

The reference point specifying unit 26 specifies a reference point by processing a past image or a current image. A reference point is a region on an image which can be extracted by image processing. For example, a reference point is the distal end of a catheter area or wire area on an image. A reference point on a past image and a reference point on a current image will be respectively referred to as a past reference point and a current reference point hereinafter.

The objective point designation unit 28 allows to manually designate an objective point on a past image with the operation unit 42. In this case, an objective point is a region which cannot be extracted or is difficult to extract by image processing. An objective point is a target arrival point of a catheter or wire on an image. Note that if an objective point can be extracted by image processing, the objective point designation unit 28 may automatically designate an objective point by image processing. An objective point associated with a past image will be referred to as a past objective point hereinafter.

The vector calculation unit 30 calculates a vector from a past reference point to a past objective point. The calculated vector represents the distance and direction from a reference point to an objective point, i.e., the relative position between a reference point and a objective point.

The relative position data storage unit 32 stores the vector data calculated by the vector calculation unit 30 and the past electrocardiographic phase data associated with the calculated vector in association with each other. More specifically, the past electrocardiographic phase to be stored is the electrocardiographic phase associated with the past image, for which a vector to be associated is calculated, in the image data storage unit 24. A combination of this vector data and past electrocardiographic phase data will be referred to as relative position data hereinafter. The relative position data storage unit 32 stores a plurality of relative position data corresponding to at least one heartbeat.

The vector specifying unit 34 specifies a specific vector among the plurality of vectors stored in the relative position data storage unit 32. A specific vector is a vector associated with a past electrocardiographic phase corresponding to the current electrocardiographic phase from the electrocardiograph 18 in the relative position data storage unit 32.

The objective point calculation unit 36 calculates the position of an objective point on a current image based on the specific vector specified by the vector specifying unit 34 and the position of the current reference point specified by the reference point specifying unit 26. The position of an objective point on a current image will be referred to as a current objective point hereinafter.

The D/A conversion unit 38 obtains an image signal for driving a display unit 40 by converting current image data into analog data. The display unit 40 is connected to the D/A conversion unit 38. The display unit 40 displays, on a monitor, the current image represented by the image signal output from the D/A conversion unit 38. At this time, the display unit 40 highlights the position of the current objective point calculated by the objective point calculation unit 36. Typically, the display unit 40 includes a plurality of monitors. For example, the display unit 40 can display past images on a monitor different from a monitor for displaying current images.

The operation unit 42 accepts various commands and information inputs from the operator or the like. As the operation unit 42, it is possible to use a pointing device such as a mouse or a trackball, a selection device such as a mode switch, or an input device such as a keyboard, as needed.

The system control unit 44 functions as the main unit of the X-ray diagnosis apparatus 1, and controls the respective units of the X-ray diagnosis apparatus 1. For example, the system control unit 44 performs current objective point display processing by controlling the respective units in response to a start signal for current objective point display processing from the operation unit 42. The system control unit 44 also performs relative position data storage processing by controlling the respective units of the image processing apparatus 20 in response to a start signal for relative position data storage processing from the operation unit 42.

A processing procedure in the X-ray diagnosis apparatus 1 which is performed under the control of the system control unit 44 will be described next. The processing according to this embodiment can be divided into relative position data storage processing performed before treatment and current objective point display processing performed during treatment. A clinical example of relative position data storage processing will be described first.

Figure 2:
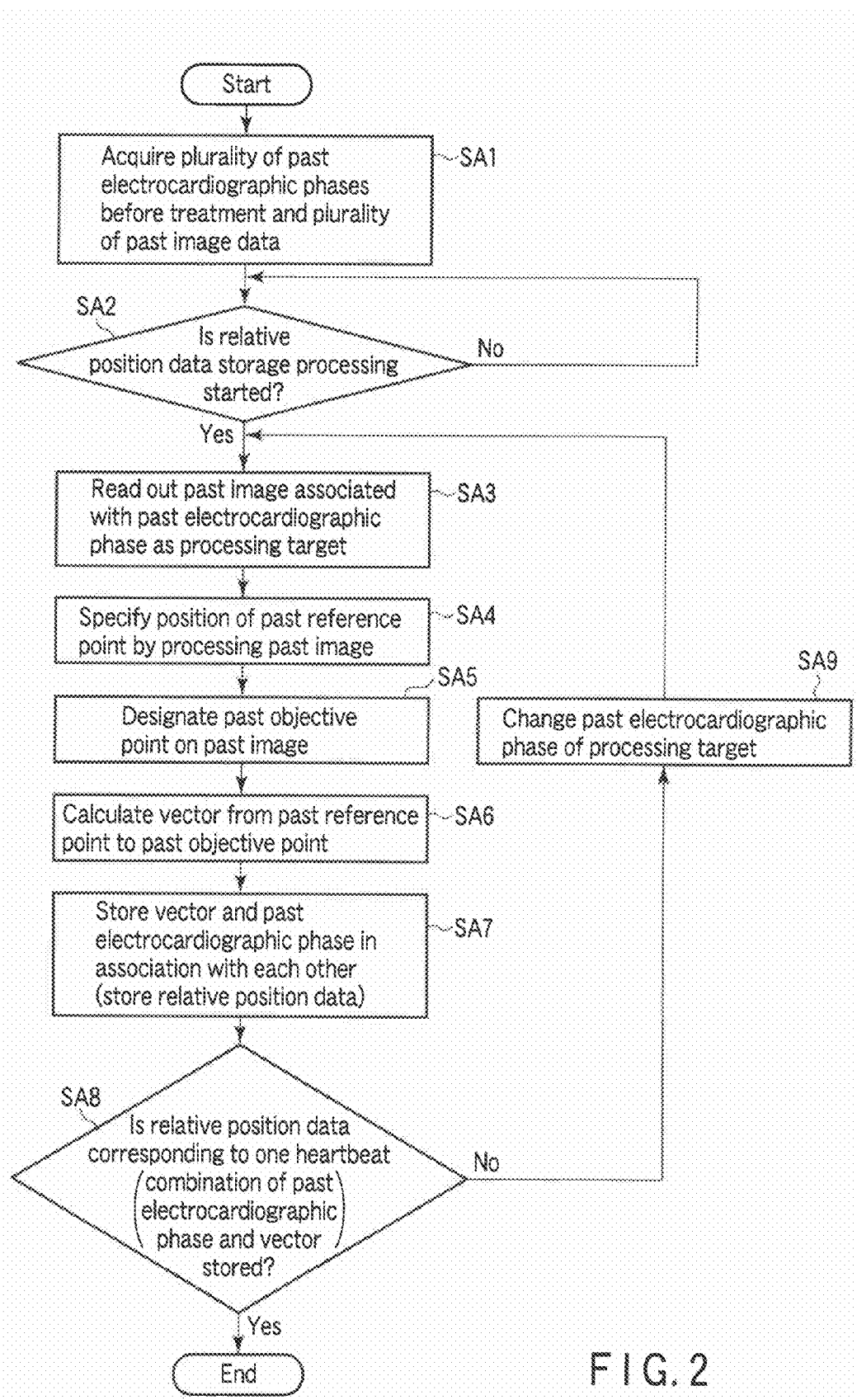
FIG. 2 is a flowchart showing a typical procedure for relative position data storage processing performed under the control of a system control unit in FIG. 1.

FIG. 2 is a flowchart showing a typical procedure for relative position data storage processing performed under the control of the system control unit 44.

Figure 3:
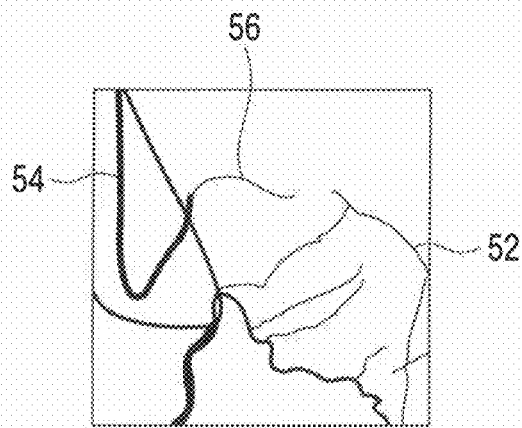
FIG. 3 is a view showing an example of a past image acquired in step SA1 in FIG. 2.

<Step SA1> First of all, the operator presses the imaging start button provided on the operation unit 42. In response to the imaging start signal supplied from the operation unit 42, the system control unit 44 controls the imaging control unit 17 to repeatedly radiograph a subject into which a contrast medium has been injected. This repeatedly generates past image data before treatment. The operator injects a contrast medium into the subject through a catheter inserted in it. As shown in FIG. 3, a generated past image therefore depicts a catheter area 54 associated with a catheter and a wire area 56 associated with a wire in addition to a blood vessel area 52 associated with a blood vessel contrast-enhanced by a contrast medium. An imaging frame rate is set in advance. The imaging frame rate is typically 15 frames/sec. This apparatus performs radiography for at least a time corresponding to one or more heartbeats. The image data storage unit 24 stores a plurality of past image data corresponding to at least one heartbeat. The electrocardiograph 18 repeatedly detects a plurality of past electrocardiographic phase data associated with the subject during radiography. The image data storage unit 24 stores each of a plurality of past electrocardiographic phase data in association with a corresponding one of past images. That is, the number of past electrocardiographic phases corresponding to one heartbeat which are to be stored is determined in accordance with the imaging frame rate. In other words, past electrocardiographic phases are discrete data. When past image data corresponding to one heartbeat are acquired, the system control unit 44 controls the imaging control unit 17 to terminate radiography in response to the imaging stop signal supplied automatically or from the operator via the operation unit 42.

<Step SA2> Upon terminating the radiography, the system control unit 44 waits for an instruction to start relative position data storage processing. When the operator issues an instruction to start via the operation unit 42 (YES in step SA2), the system control unit 44 starts relative position data storage processing.

<Step SA3> In the relative position data storage processing, the system control unit 44 reads out first the past image data as a processing target from the plurality of past images stored in the image data storage unit 24. The past image as the processing target is, for example, a past image associated with a preset past electrocardiographic phase. The system control unit 44 supplies the readout past image data to the reference point specifying unit 26.

<Step SA4> Upon reading out the past image, the system control unit 44 causes the reference point specifying unit 26 to perform past reference point specifying processing. The reference point specifying unit 26 processes the past image as the processing target to specify the position of a reference point on the past image. Typically, the reference point specifying unit 26 specifies the distal end of the catheter area depicted on the past image as a past reference point.

In the image processing, first of all, the reference point specifying unit 26 performs subtract background processing for the past image as the processing target, histogram stretching processing for the past image having undergone the subtract background processing, threshold processing for the past image having undergone the histogram stretching processing, erosion processing for the past image having undergone the threshold processing, and dilation processing for the past image having undergone the erosion processing.

Note that the subtract background processing is image processing for smoothing a background area. The histogram of the image having undergone the subtract background processing is shifted toward a bright area (high pixel values) as compared with a histogram before the processing. The histogram stretching processing is image processing for stretching the histogram to correct the histogram shifted toward the bright area. A catheter area is located in a dark area (low pixel values) on the histogram. The threshold processing uses this to leave those of all the pixels constituting the past image having undergone the histogram stretching processing which have pixel values corresponding to the catheter area and remove the remaining pixels. The past image having undergone the threshold processing includes a plurality of isolated points (noise) as well as the catheter area. The erosion processing uses a Minkowski difference to erase the isolated points from the past image having undergone the threshold processing. This erosion processing erases the edge of the catheter area as well as the isolated points. As a consequence the catheter area becomes narrow. The dilation processing uses a Minkowski sum to restore the thickness of the catheter area on the past image having undergone the erosion processing to the thickness of the catheter area before the erosion processing.

Figure 4:
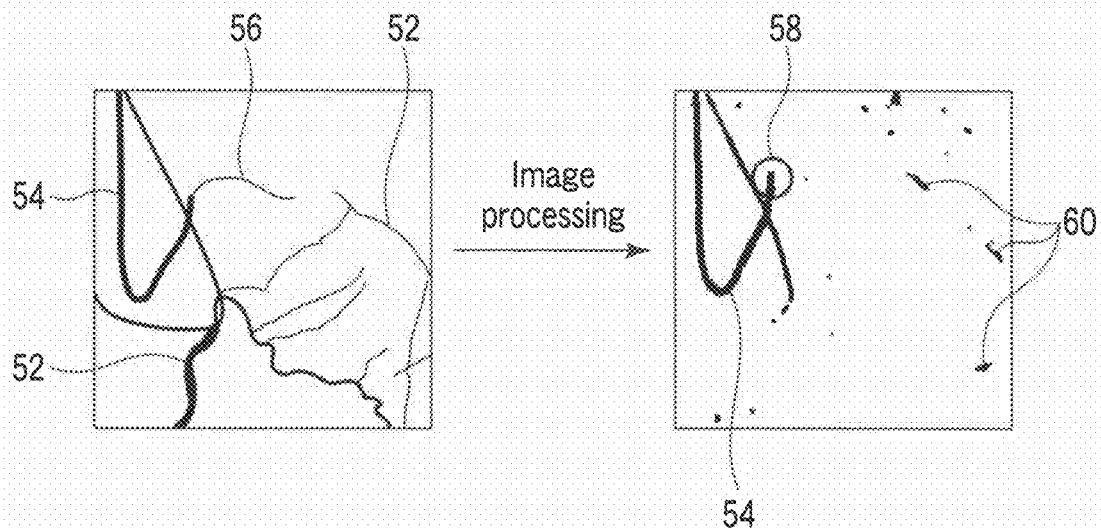
FIG. 4 is a view for explaining past reference point specifying processing performed in step SA4 in FIG. 2.

With these series of image processing, as shown in FIG. 4, the catheter area 54 is extracted from the past image. A distal end portion 58 of the extracted catheter area 54 is specified as a past reference point. The reference point specifying unit 26 supplies the coordinate data of the specified past reference point 58 to the vector calculation unit 30.

Note that even a past image having undergone these series of image processing may include isolated points 60 irrelevant to the catheter area 54. This is because the blood vessel area 52 also has a thickness or pixel value similar to that of the catheter area 54. In this case, it is possible to make the display unit 40 display a past image after image processing and make the operator designate a reference point on the displayed past image via the operation unit 42. It is also possible to make the operator designate a reference point on a past image before image processing.

Note that the above series of image processing have been described as an example of a catheter area extraction method. It is therefore not always necessary to perform all the image processing described above as long as a catheter area can be extracted without performing all the image processing. For example, it is possible to extract a catheter area by only threshold processing.

<Step SA5> Upon specifying a past reference point, the system control unit 44 causes the objective point designation unit 28 to perform past objective point designation processing. As shown in FIG. 5, the objective point designation unit 28 designates a past objective point at a point 62 designated by the operator via the operation unit 42. The objective point designation unit 28 supplies the coordinate data of the designated objective point 62 to the vector calculation unit 30.

As shown in FIG. 5, a objective point is, for example, the exit of a stenotic region of a CTO (Chronic Total Occlusion). A stenotic region of a CTO is a stenotic region which is chronically totally occluded. A portion near the exit of the stenotic region of the CTO is not depicted unless being contrast-enhanced.

Another objective point is a stenotic region in which a stent is indwelled. The stenotic region is not depicted on an image unless being contrast-enhanced.

Still another objective point can be a branch point of a blood vessel. A branch point of a blood vessel is not depicted unless being contrast-enhanced.

Still another objective point is, for example, an end portion of a bioabsorbable stent such as a polymer stent. In general, a stent is detachably mounted on the distal end portion of a catheter. Portions corresponding to the two ends of the stent on the catheter are attached with marks which are visible on an X-ray image. The stent is inserted up to an indwelling region through the catheter and is inflated in the dwelling region. After inflation, the operator removes the catheter together with the marks. If a stenotic region is large, two stents are inserted sometimes. The second stent should be inserted near the place where the first stent is inserted. However, since the marks have been removed, the operator cannot visually recognize the position of the first stent on the X-ray image. For this reason, an objective point is designated at an end of the first stent as a target arrival point for the second stent.

Still another objective point is a stent other than a bioabsorbable stent, such as a BMS (Bare Metal Stent) or DES (Drug Eluting Stent). These stents are difficult to visually recognize on an X-ray image generated by X-ray fluoroscopy. In order to improve the visibility of such a stent, radiography with a larger dose of X-rays than X-ray fluoroscopy is used sometimes. An increase in dose, however, will increase the load on a subject. In order to improve the visibility of the stent without increasing the load on the subject, for example, an objective point is designated at an end portion of the stent.

Note that the designation method to be used is not specifically limited. For example, the operator can designate a desired point on a past image displayed on the display unit 40 via the mouse. The operator can also designate an objective point with coordinates via numeric keypad. The operator can also designate an objective point by moving a mark to a desired point on a past image via arrow keys and pressing a specific key. Alternatively, the operator can designate an objective point by directly touching a desired point via a touch panel.

<Step SA6> When a past objective point is designated, the system control unit 44 causes the vector calculation unit 30 to perform vector calculation processing. As shown in FIG. 6, the vector calculation unit 30 calculates a vector from the past reference point 58 to the past objective point 62 on the past image. The vector calculation unit 30 supplies the calculated vector data to the relative position data storage unit 32.

<Step SA7> Upon calculating the vector, the system control unit 44 causes the relative position data storage unit 32 to perform storage processing. As shown in FIG. 7, the relative position data storage unit 32 stores the vector data in association with the past electrocardiographic phase associated with a past image as a processing target. That is, the relative position data storage unit 32 stores relative position data corresponding to one electrocardiographic phase.

<Step SA8> Upon storing the relative position data, the system control unit 44 determines whether the relative position data storage unit 32 has stored relative position data corresponding to one heartbeat.

<Step SA9> Upon determining in step SA8 that the relative position data storage unit 32 has not stored relative position data corresponding to one heartbeat (NO in step SA8), the system control unit 44 changes the past image as the processing target into a past image associated with the next past electrocardiographic phase.

The system control unit 44 repeats steps SA3 to SA7 for the changed processing target in the same manner as described above. In this manner, the relative position data storage unit 32 stores the relative position data corresponding to one heartbeat. In other words, the relative position data is discrete data. Upon determining in step SA8 that relative position data corresponding to one heartbeat is stored (YES in step SA8), the system control unit 44 terminates the relative position data storage processing.

Figure 8:
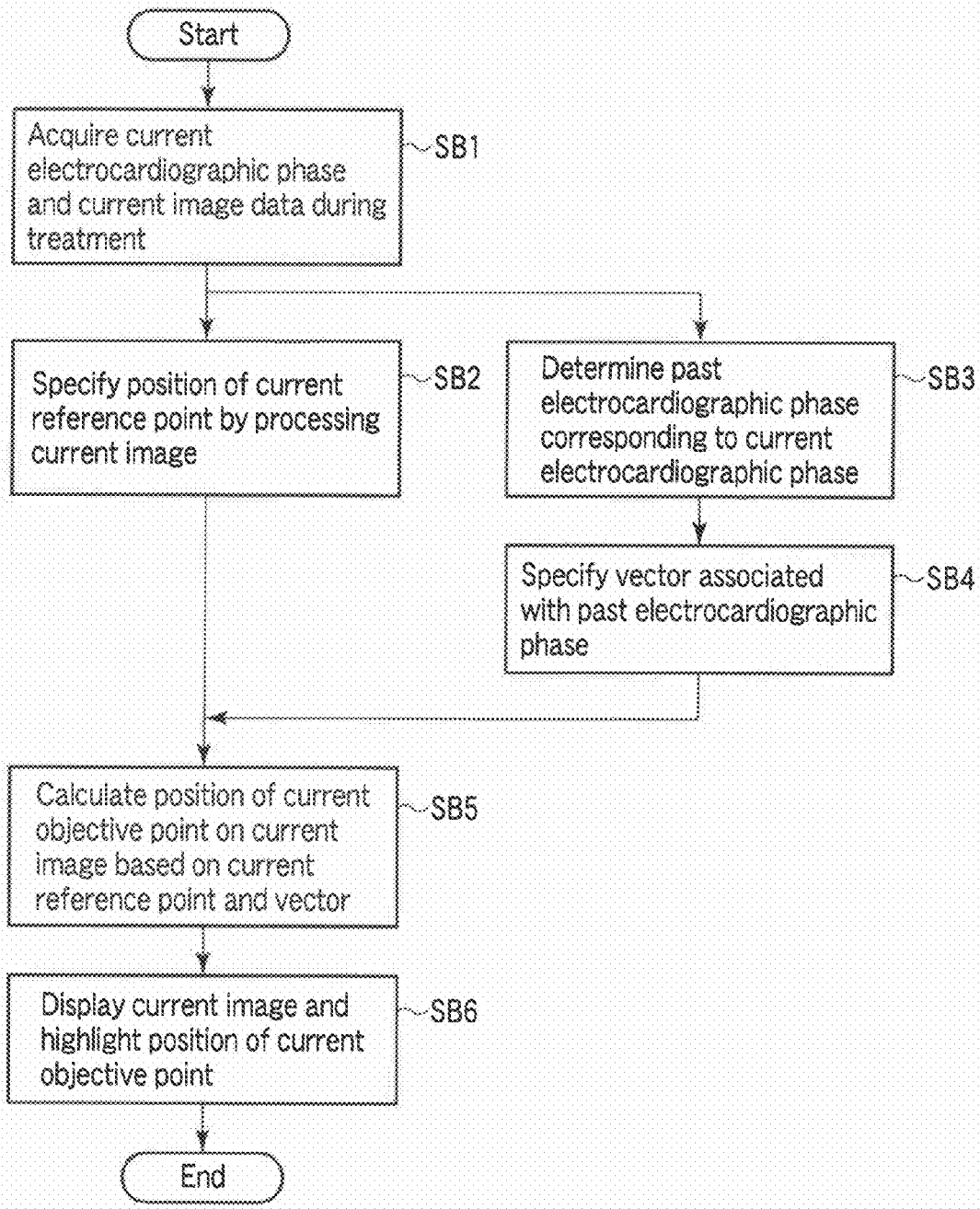
FIG. 8 is a flowchart showing a typical procedure for current objective point display processing performed under the control of the system control unit in FIG. 1.

A clinical example of current objective point display processing performed during treatment will be described next. FIG. 8 is a flowchart showing a typical procedure for current objective point display processing performed under the control of the system control unit 44.

<Step SB1> First of all, in response to the imaging start signal supplied from the operator or the like via the operation unit 42, the system control unit 44 controls the imaging control unit 17 to repeatedly radiograph the subject, into which no contrast medium has been injected. With this operation, current image data associated with treatment are repeatedly generated. During radiography, the operator advances the catheter to a treatment region in the subject. As shown in FIG. 9, therefore, the generated current image depicts the catheter area 54 and the wire area 56. However, since no contrast medium has been injected into the subject, the current image does not depict a treatment region such as a stenotic region. The imaging frame rate is determined in advance, which is typically 15 frames/sec. The image data storage unit 24 stores the generated current image data. Note that the position of the subject during radiography for a current image coincides with the position of the subject during radiography for a past image. In addition, the imaging angle during radiography for the current image coincides with the imaging angle during radiography for the past image. Assume therefore that the current image and the past image have already been positioned. During radiography, the electrocardiograph 18 repeatedly detects the current electrocardiographic phase data associated with the subject. The image data storage unit 24 stores the current electrocardiographic phase data in association with the current image.

<Step SB2> Upon acquiring the current image and current electrocardiographic phase data, the system control unit 44 causes the reference point specifying unit 26 to perform current reference point specifying processing in real time. The reference point specifying unit 26 reads out the current image stored in the image data storage unit 24, and processes the readout current image to specify the position of the current reference point on the current image. Typically, the reference point specifying unit 26 specifies the distal end of the catheter area depicted on the current image as a current reference point. Note that the contents of this image processing are the same as those of the image processing for specifying the past reference point in step SA4, and hence a description of the processing will be omitted.

<Step SB3> Along with step SB2, the system control unit 44 causes the vector specifying unit 34 to perform past electrocardiographic phase determination processing. First of all, the vector specifying unit 34 reads out a current image stored in the image data storage unit 24, and specifies the current electrocardiographic phase associated with the readout current image. The vector specifying unit 34 determines a past electrocardiographic phase corresponding to the specified current electrocardiographic phase among the plurality of past electrocardiographic phases stored in the relative position data storage unit 32. If there is a past electrocardiographic phase coinciding with the current electrocardiographic phase, the coincident past electrocardiographic phase is determined as a past electrocardiographic phase corresponding to the current electrocardiographic phase. If there is no past electrocardiographic phase coinciding with the current electrocardiographic phase, a past electrocardiographic phase having an electrocardiographic phase closest to the current electrocardiographic phase is determined as a past electrocardiographic phase corresponding to the current electrocardiographic phase.

<Step SB4> Upon determining a past electrocardiographic phase, the vector specifying unit 34 specifies a vector associated with the determined past electrocardiographic phase in the relative position data storage unit 32. The vector specifying unit 34 supplies the specified vector data to the objective point calculation unit 36.

<Step SB5> Upon specifying a current reference point and a vector, the system control unit 44 causes the objective point calculation unit 36 to perform current objective point position calculation processing. The objective point calculation unit 36 calculates the position of the current objective point based on the coordinates of the current reference point and the specified vector. More specifically, as shown in FIG. 10, the objective point calculation unit 36 matches the start point of a specified vector 66 with a current reference point 68, and sets the position indicated by the vector 66 as a current objective point 70. In this manner, using the vector 66 can calculate the position of the current objective point 70 as a relative position from the current reference point 68. The objective point calculation unit 36 supplies the position of the current objective point 68 to the D/A conversion unit 38.

<Step SB6> Upon calculating the position of the current objective point, the system control unit 44 causes the display unit 40 to performed current objective point display processing. The D/A conversion unit 38 reads out current image data from the image data storage unit 24, converts the readout current image data into analog data, and supplies the analog current image data to the display unit 40. As shown in FIG. 11, the display unit 40 highlights the calculated position of the current objective point while displaying the supplied current image. That is, the display unit 40 displays the position of the current objective point on the current image. Methods of highlighting a current objective point include a method of displaying the position of the current objective point with a luminance, lightness, or color different from that of other portions, and a method of displaying a current objective point with a mark such as an arrow.

Highlighting a current objective point on a current image may interfere with the operation of a device such as a catheter. For this reason, a user interface for selecting whether to highlight a current objective point can be provided for the operation unit 42. For example, the operation unit 42 can include a switch for selecting whether to highlight.

Steps SB1 to SB7 are repeatedly performed in real time every time a current image is generated. The operator can therefore visually recognize the current position of the catheter and the current objective point as the target arrival point of the catheter on a moving image by observing only the current image.

Note that the method of specifying a current reference point in step SB2 is not limited to the above method. For example, the reference point specifying unit 26 may track a current reference point specified for one current electrocardiographic phase to specify a current reference point associated with another current electrocardiographic phase. Tracking methods include, for example, pattern matching processing which uses the movement of a past reference point as a pattern.

In addition, the vector used for the calculation of a current objective point in step SB5 is a vector associated with a past electrocardiographic phase corresponding to a current electrocardiographic phase. However, this embodiment is not limited to this. For example, a vector used for the calculation of a current objective point can be a predetermined vector. In this case, current objective point highlighting processing can be used for a region with little body movement, e.g., the brain.

The display accuracy of the position of a current objective point will be examined next. The present inventor performed simulation to compare the display accuracy of a current objective point according to this embodiment with the display accuracy according to the prior art. This simulation used four current images, namely a current image A, a current image B, a current image C, and a current image D. These four current images were generated in the order of A→B→C→D in identical electrocardiographic phases. In addition, the current images A and C were in identical respirator phases (i.e., phases in which the position of the diaphragm of the subject remained the same). A current reference point was set at the distal end of a catheter, and a current objective point was set at the exit of a stenotic region of a CTO, to which this technique is mainly applied in clinical cases. Note that as a conventional technique, a general conventional ECG technique was used. The conventional ECG technique is a technique of using a past image (contrast-enhanced blood vessel image) corresponding to one heartbeat to display a past image in an electrocardiographic phase identical or close to that of a current image (fluoroscopic image) on the current image by ECG. In this case, the user needs to determine by himself/herself a objective point such as a blood vessel.

Figure 12:
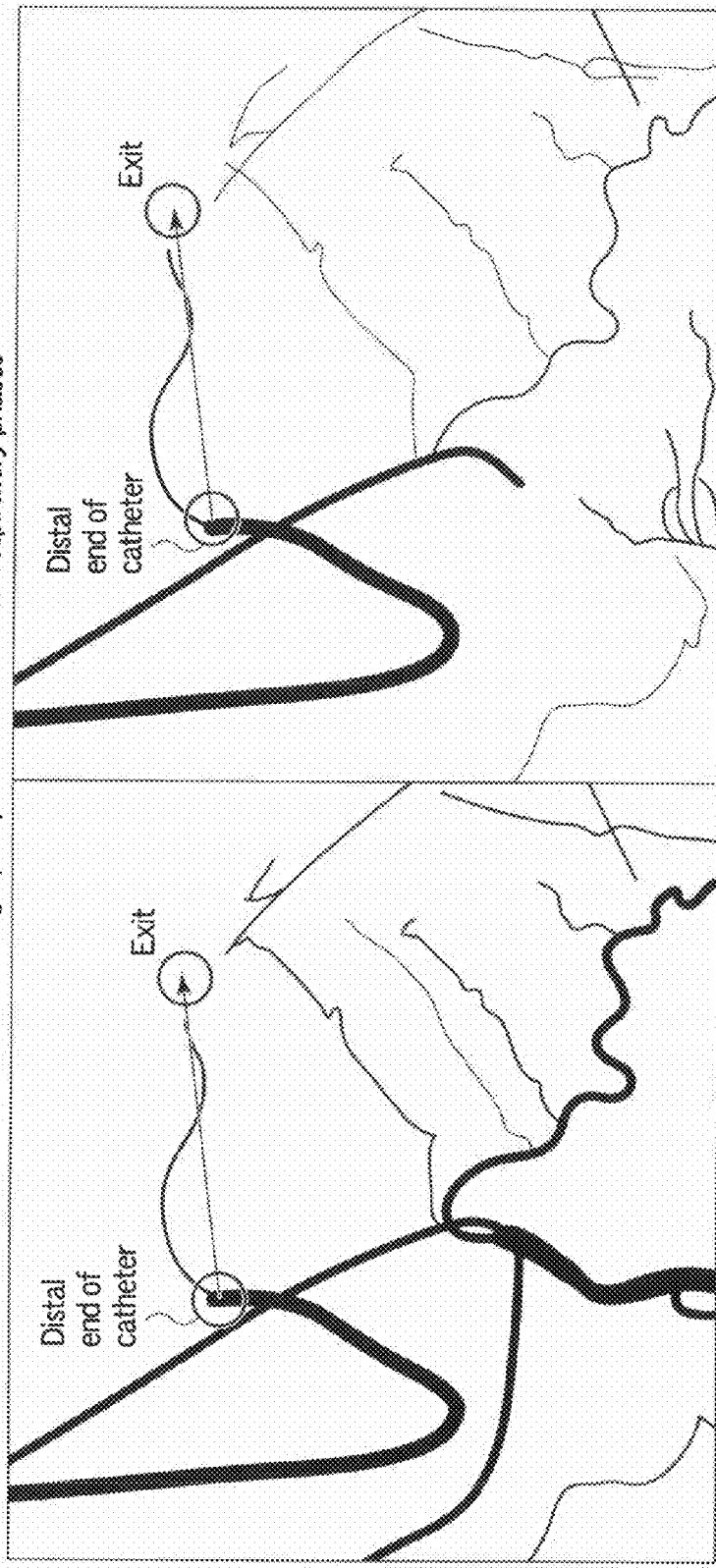
FIG. 12 is a view showing the comparison result on objective point display accuracy between a technique according to this embodiment and a prior art.

The result obtained by comparing the display accuracies of current objective points using the current images A and C in identical electrocardiographic phases and identical respiratory phases will be described first. As shown in FIG. 12, the coordinates of the distal end of the catheter (current reference point) on the current image A were (x, y)=(173, 162), and the coordinates of the exit of a stenotic region of a CTO (current point of interest) were (x, y)=(376, 137). Likewise, the coordinates of the distal end of the catheter on the current image C were (x, y)=(171, 148), and the coordinates of the exit of a stenotic region of a CTO were (x, y)=(370, 124). The difference between the coordinates of the distal end of the catheter on the current image A and those on the current image C was (x, y)=(−2, −14), and the difference between the coordinates of the exit of the stenotic region on the current image A and those on the current image C was (x, y)=(−6, −13). A vector A from the distal end of the catheter to the exit of the stenotic region on the current image A was (x, y)=(203, −25). A vector C from the distal end of the catheter to the exit of the stenotic region on the current image C was (x, y)=(199, −24). The difference between the vector on the current image A and the vector on the current image C was (x, y)=(−4, 1).

As shown in FIG. 13, the above data indicates that a distance (shift) corresponding to the difference between the coordinates of the exit of the stenotic region on the current image A and the coordinates of the exit of the stenotic region on the current image C is 14.32 pixels. On the other hand, a distance (shift) corresponding to the difference between the vector A on the current image A and the vector C on the current image C is 4.12 pixels. By the way, ideally each distance should be 0 pixel. This result indicates that the distance (shift) corresponding to the difference between the vectors is smaller than the distance (shift) corresponding to the difference between the coordinates. That is, as for the exit of the stenotic region in manipulation at the CTO, the distance (shift) can be reduced by 71%. This result indicates that the technique according to this embodiment which displays a current objective point by using a vector from a current reference point is higher in objective point display accuracy than the conventional technique of simply superimposing images.

The result obtained by comparing the display accuracies of current objective points using the current images A and B in identical electrocardiographic phases and different respiratory phases will be described next. As shown in FIG. 14, the difference between the coordinates of the distal end of the catheter on the current image A and those on the current image B was (x, y)=(0, 17), and the difference between the coordinates of the exit of the stenotic region on the current image A and those on the current image B was (x, y)=(2, 18). Therefore, a distance (shift) corresponding to the difference between the coordinates of the exit of the stenotic region on the current image A and the coordinates of the exit of the stenotic region on the current image B was 18.11 pixels. The difference between the vector from the current reference point to the current objective point on the current image A and the vector from the current reference point to the current objective point on the current image B was (x, y)=(2, 1). Therefore, a distance (shift) corresponding to the difference between the vector on the current image A and the vector on the current image B is 2.24 pixels. That is, in the case of the current images A and B, as for the exit of the stenotic region in manipulation at the CTO, the shift can be reduced by 88%.

As shown in FIG. 15, the result obtained by comparing the display accuracies of current objective points on the current images A and D in identical electrocardiographic phases and different respiratory phases exhibited the same tendency as shown in FIG. 14. That is, in the case of the current images A and D, as for the exit of the stenotic region in manipulation at the CTO, the distance (shift) can be reduced by 84%.

The two results in FIGS. 14 and 15 exhibit that even in identical electrocardiographic phases and different respiratory phases, the technique according to this embodiment is higher in objective point display accuracy than the prior art (conventional ECG technique).

Figure 16:
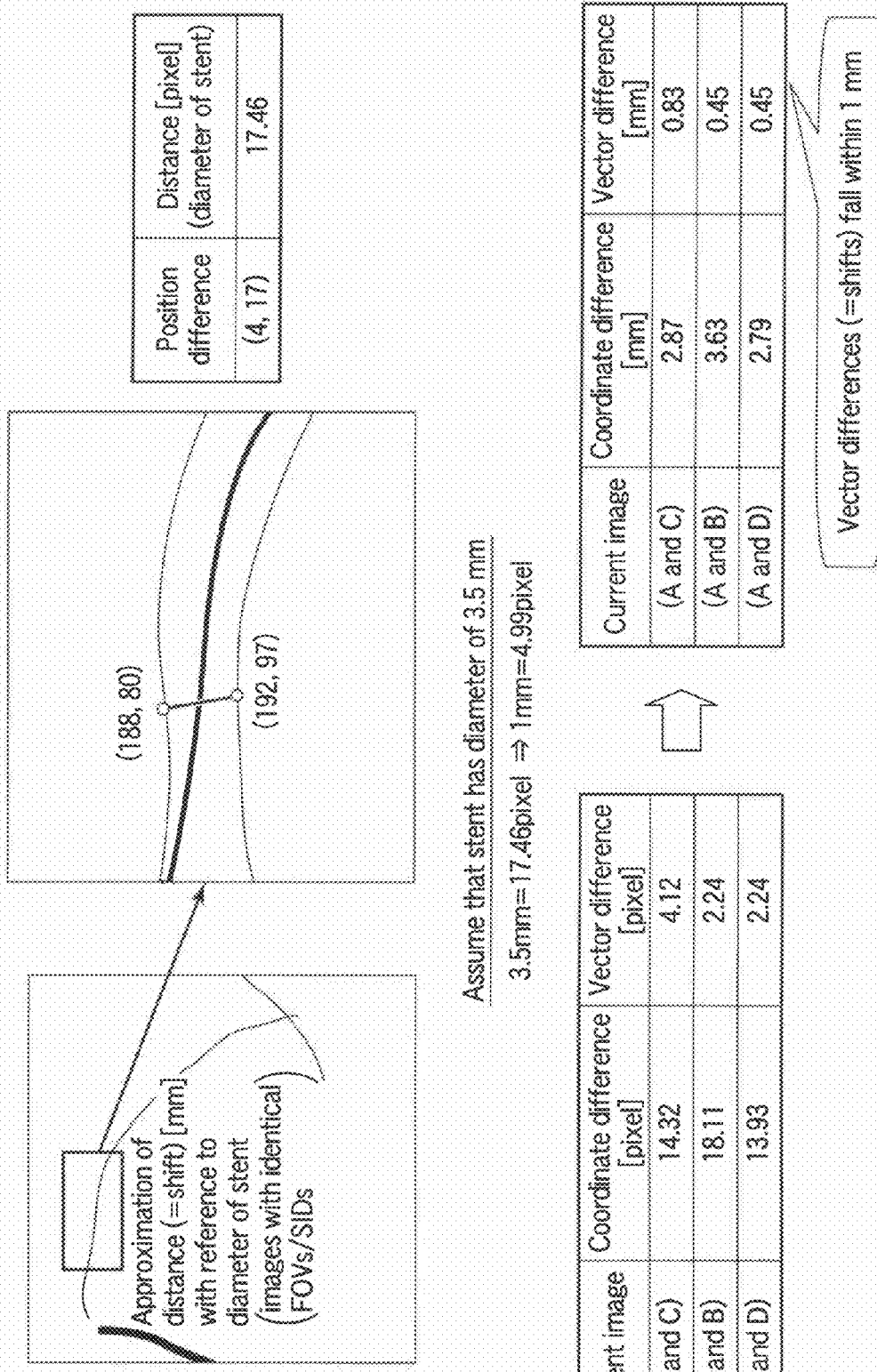
FIG. 16 is a view showing a concrete example of a case in which the actual shift amount of a current objective point based on the technique according to this embodiment falls within an allowable range in a clinical term.

A concrete example of a case in which the actual shift amount of a current objective point based on the technique according to this embodiment falls within an allowable range in a clinical term will be described next with reference to FIG. 16. The images used in FIG. 16 are images associated with the current images A to D after operation (stent indwelling). The FOV (the size of the field of view) of this image is equal to that of the current images A to D.

Stent indwelling is very delicate operation. The operator therefore demands very strict stent position display accuracy. More specifically, a shift of 1 mm or more makes this technique useless from the clinical viewpoint. It is therefore proper to set a clinical allowable range to 1 mm or less for the actual shift amount of a current objective point.

As shown in FIG. 16, the coordinates of the two end portions of the stent on the current image in the thickness direction were (x, y)=(188, 80) and (x, y)=(192, 97), respectively. Therefore, the stent diameter corresponds to 17.46 pixels. Assume that the stent diameter is 3.5 mm. In this case, the correspondence relationship represented by 3.5 mm=17.46 pixels holds. According to this correspondence relationship, 1 mm=4.99 pixels.

As described above, the coordinate difference between the current objective point on the current images A and C was 14.32 pixels, and the vector difference was 4.12 pixels. Likewise, the coordinate difference between the current point of interests on the current images A and B was 18.11 pixels, and the vector difference was 2.24 pixels. The coordinate difference between the current objective point on the current images A and D was 13.93 pixels, and the vector difference was 2.24 pixels.

According to the above correspondence relationship, therefore, the actual distances corresponding to the coordinate differences and vector differences between the current objective points are follows. The coordinate difference between the current objective points on the current images A and C is 2.87 mm, and the vector difference is 0.83 mm. The coordinate difference between the current objective points on the current images A and B is 3.63 mm, and the vector difference is 0.45 mm. The coordinate difference between the current points of interest on the current images A and D is 2.79 mm, and the vector difference is 0.45 mm. This result reveals that the vector differences in all the cases fall within the allowable range, i.e., within 1 mm. The technique according to this embodiment therefore has accuracy that meets clinical demands, and is sufficiently feasible.

With the above arrangement, the X-ray diagnosis apparatus 1 accurately displays an objective point such as a stenotic region on a current image (fluoroscopic image). This makes it unnecessary for the operator to comprehend the position of an objective point by alternately seeing a past image (contrast-enhanced image) and a current image displayed on different monitors. In addition, since the number of times of contrast medium imaging decreases as compared with the prior art, the load on each patient decreases. This allows the X-ray diagnosis apparatus 1 according to this embodiment to improve the efficiency of catheterization.

(Modification)

In step SB4 in this embodiment, the system control unit 44 determines a vector which is associated with a past electrocardiographic phase coinciding with or adjacent to a current electrocardiographic phase. In the modification to be described below, when a current electrocardiographic phase does not coincide with a past electrocardiographic phase, a vector is interpolated based on the two vectors associated with the two past electrocardiographic phases adjacent to each other through the current electrocardiographic phase.

Figure 17:
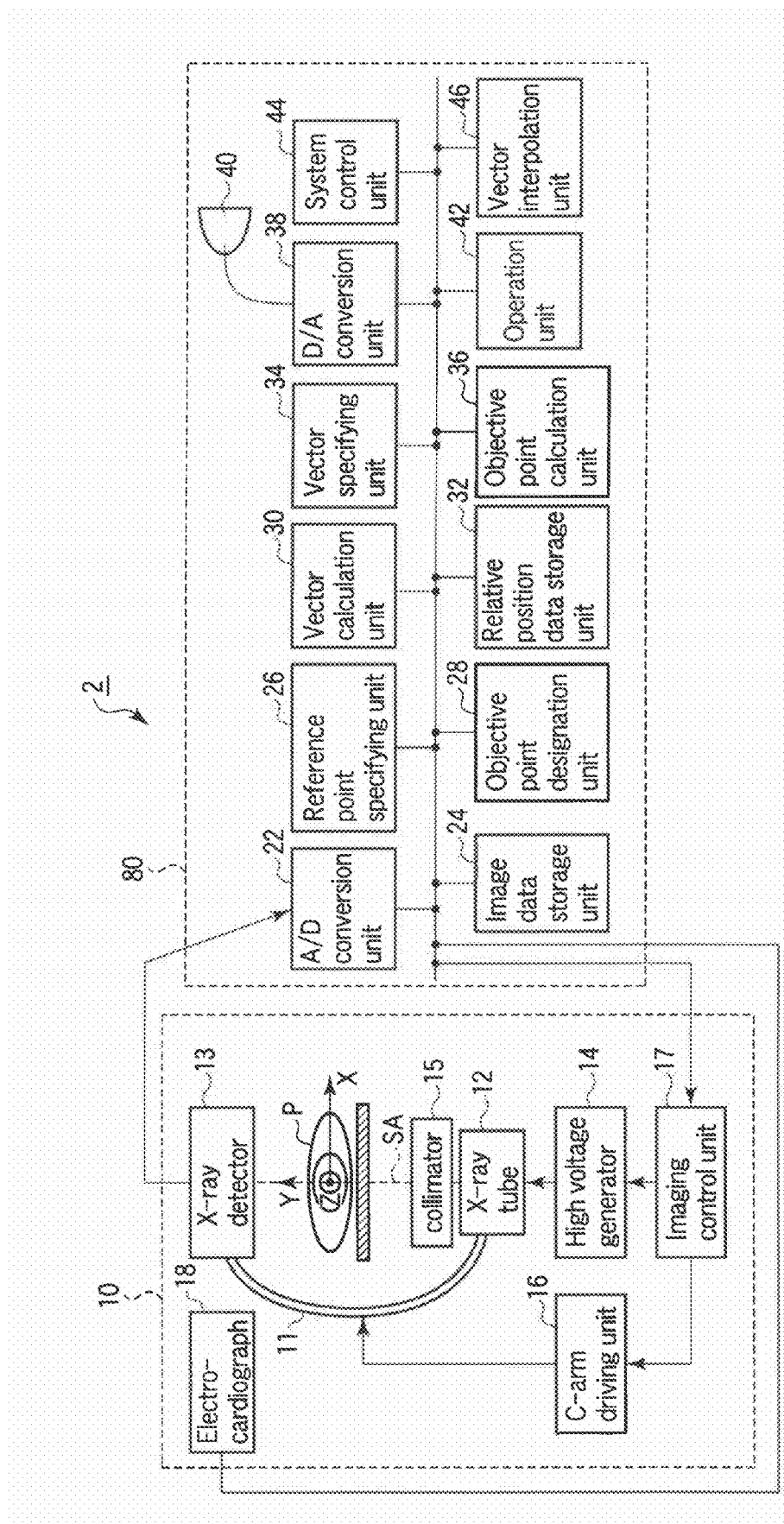
FIG. 17 is a block diagram showing the arrangement of an X-ray diagnosis apparatus according to a modification of this embodiment.

FIG. 17 is a block diagram showing the arrangement of an X-ray diagnosis apparatus 2 according to the modification of this embodiment. As shown in FIG. 17, the X-ray diagnosis apparatus 2 according to the modification further includes a vector interpolation unit 46. The vector interpolation unit 46 interpolates a vector corresponding to a current electrocardiographic phase based on the two vectors associated with the two past electrocardiographic phases adjacent to each other through the current electrocardiographic phase.

A clinical example of current objective point display processing according to the modification performed under the control of the system control unit 44 will be described next. FIG. 18 is a flowchart showing a typical procedure for current objective point display processing according to the modification.

<Step SC1> When the vector calculation unit 30 determines in step SB3 that there is no past electrocardiographic phase coinciding with a current electrocardiographic phase among the plurality of past electrocardiographic phases stored in the relative position data storage unit 32, the system control unit 44 causes the vector interpolation unit 46 to perform processing for specifying two past electrocardiographic phases. The vector interpolation unit 46 specifies two past electrocardiographic phases adjacent to each other through the current electrocardiographic phase among the plurality of past electrocardiographic phases stored in the relative position data storage unit 32.

<Step SC2> When the two past electrocardiographic phases are specified, the system control unit 44 causes the vector interpolation unit 46 to perform vector specifying processing. The vector interpolation unit 46 specifies two vectors associated with the two specified past electrocardiographic phases in the relative position data storage unit 32.

<Step SC3> When two vectors are specified, the system control unit 44 performs vector interpolation processing. The vector interpolation unit 46 interpolates a vector associated with a past electrocardiographic phase coinciding with the current electrocardiographic phase based on the two specified vectors. Interpolation processing is performed to set the vector at, for example, the average or median value of the two vectors. When interpolation with higher accuracy is required, it is possible to interpolate the vector based on the two vectors and two past electrocardiographic phases corresponding to them. Any existing interpolation methods can be used, including a linear interpolation method, a spline interpolation method, a Lagrange interpolation method, and a least squares method. The vector interpolation unit 46 supplies the interpolated vector data to the objective point calculation unit 36.

When the vector is interpolated, steps SB5 and SB6 in FIG. 8 are performed in the order named.

Note that since the vector interpolation unit 46 can interpolate vectors, it is possible to decrease the number of relative position data (vectors) to be stored in the relative position data storage unit 32 in advance as compared with the above embodiment. For example, the operator may be allowed to select a past image as a calculation target for relative position data via the operation unit 42. More specifically, the operator is allowed to select a past electrocardiographic phase as a calculation target for relative position data via the operation unit 42. The operator can arbitrarily set the number of past electrocardiographic phases to be selected via the operation unit 42. More specifically, as shown in FIG. 19, it suffices if the operator selects electrocardiographic phases at about five points (e.g., a start time θ1 of a P wave, an end time θ2 of a QRS wave, a start time θ3 of a T wave, an end time θ4 of a T wave, and an end time θ5 of a U wave) within one heartbeat. This decreases the number of relative position data as calculation targets, thus saving the trouble of designating a objective point.

As described above, the X-ray diagnosis apparatus 2 according to the modification of this embodiment can improve the efficiency of catheterization.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray diagnosis apparatus comprising:
an imaging unit configured to comprise an X-ray tube and a detector to obtain a first X-ray image and a second X-ray image associated with a subject in which a medical tool is inserted;
a first specifying unit configured to specify a first reference point on a first medical tool area included in the first X-ray image;
a designation unit configured to designate a first objective point on the first X-ray image;
a first calculation unit configured to calculate a relative positional relationship between the first reference point and the first objective point;
a second specifying unit configured to specify a second reference point on a second medical tool area included in the second X-ray image;
a second calculation unit configured to calculate a position of a second objective point on the second X-ray image based on the relative positional relationship and the second reference point; and
a display unit configured to display the second X-ray image while highlighting the position of the second objective point.

2. The apparatus according to claim 1, wherein the designation unit configured to designate the first objected point on the first X-ray image in accordance with one of an instruction from a user and image processing.

3. The apparatus according to claim 1, wherein
the first specifying unit configured to specify the first reference point included in the first X-ray image by image processing, and
the second specifying unit configured to specify the second reference point included in the second X-ray image by image processing.

4. The apparatus according to claim 1, wherein the display unit configured to display a mark at the position of the second objective point on the second X-ray image.

5. The apparatus according to claim 1, wherein
the first X-ray image is an X-ray image depicting one of a treatment region of a blood vessel which is contrast-enhanced by a contrast medium, a branch point of a blood vessel which is contrast-enhanced by a contrast medium, or a mark for a bioabsorbable stent, and
the second X-ray image is an X-ray image which depicts none of the treatment region, the branch point, or the mark.

6. The apparatus according to claim 1, further comprising a storage unit which stores the relative position information.

7. An X-ray diagnosis apparatus comprising:
a storage unit configured to store a plurality of vectors and a plurality of past electrocardiographic phases in association with each other, each of the plurality of vectors being a vector from a past reference point to a past objective point included in each of a plurality of past images associated with a subject, and each of the plurality of past electrocardiographic phases being an electrocardiographic phase of the subject which is associated with a time at which the past image was obtained;
an imaging unit configured to comprise an X-ray tube and a detector to obtain a current image associated with the subject;
a first specifying unit configured to specify a current reference point on the current image by image processing;
a detection unit configured to detect a current electrocardiographic phase associated with the current image;
a second specifying unit configured to specify a specific vector associated with a past electrocardiographic phase corresponding to the detected current electrocardiographic phase among the plurality of vectors;
a first calculation unit configured to calculate a position of a current objective point on the current image based on the specified vector and the position of the current reference point; and
a display unit configured to display the position of the current objective point on the current image.

8. The apparatus according to claim 7, further comprising a third specifying unit configured to specify the past reference point by processing each of the plurality of past images.

9. The apparatus according to claim 7, further comprising a designation unit configured to designate the past objective point in accordance with one of processing each of the plurality of past images and an instruction from a user.

10. The apparatus according to claim 7, further comprising a second calculation unit configured to calculate the vector from the past reference point to the past objective point for each of the plurality of past images.

11. The apparatus according to claim 7, further comprising an interpolation unit configured to interpolate a vector associated with an electrocardiographic phase between the two past electrocardiographic phases based on two vectors of the plurality of vectors, the two vectors are associated with two temporally adjacent past electrocardiographic phases.

12. The apparatus according to claim 7, wherein the storage unit configured to store only a predetermined past electrocardiographic phase of the plurality of past electrocardiographic phases and a vector associated with the predetermined past electrocardiographic phase.

13. The apparatus according to claim 7, wherein the display unit configured to display a mark at the position of the current objective point.

14. The apparatus according to claim 7, wherein
the past image is an X-ray image depicting one of a treatment region of a blood vessel which is contrast-enhanced by a contrast medium, a branch point of a blood vessel which is contrast-enhanced by a contrast medium, or a mark for a bioabsorbable stent, and
the current image is an X-ray image which depicts none of the treatment region, the branch point, or the mark.

* * * * *